United States Patent
Herrmann et al.

(10) Patent No.: US 8,804,113 B2
(45) Date of Patent: Aug. 12, 2014

(54) COVER VIEW GRIPPER

(75) Inventors: Jürgen Herrmann, Rosenheim (DE); Marius Michael Herrmann, Rosenheim (DE)

(73) Assignee: KHS GmbH, Dortmund (DE)

(*) Notice: Subject to any disclaimer, the term of this patent is extended or adjusted under 35 U.S.C. 154(b) by 31 days.

(21) Appl. No.: 13/580,467

(22) PCT Filed: Dec. 9, 2010

(86) PCT No.: PCT/EP2010/007501
§ 371 (c)(1),
(2), (4) Date: Aug. 22, 2012

(87) PCT Pub. No.: WO2011/113463
PCT Pub. Date: Sep. 22, 2011

(65) Prior Publication Data
US 2012/0314213 A1    Dec. 13, 2012

(30) Foreign Application Priority Data

Mar. 19, 2010 (DE) .................. 10 2010 012 214

(51) Int. Cl.
*G01N 21/00* (2006.01)
(52) U.S. Cl.
USPC ............... 356/240.1; 356/239.4; 356/239.7
(58) Field of Classification Search
USPC ............ 356/237.1–241.6, 242.1–243.8, 356/426–431, 600–640
See application file for complete search history.

(56) References Cited

U.S. PATENT DOCUMENTS

| | | | |
|---|---|---|---|
| 3,479,514 A | | 11/1969 | Kidwell |
| 3,557,950 A | * | 1/1971 | Powers .................. 209/526 |
| 3,944,058 A | * | 3/1976 | Strauss ................ 198/377.07 |
| 4,323,158 A | * | 4/1982 | Wheaton et al. .......... 209/524 |
| 5,398,898 A | * | 3/1995 | Bever .................... 248/154 |
| 6,072,575 A | | 6/2000 | Loll |

FOREIGN PATENT DOCUMENTS

| | | |
|---|---|---|
| DE | 3 308 489 A1 | 9/1984 |
| DE | 20 2005 00675 | 10/2005 |
| DE | 10 2007 025 520 | 12/2008 |
| DE | 10 2009 00364 | 9/2010 |
| EP | 0 873 510 B1 | 2/2006 |
| JP | 2 273 983 | 11/1990 |
| JP | 3257356 | 2/1997 |
| JP | 2001080802 | 3/2001 |
| JP | 2009/069099 | 4/2009 |
| WO | WO 03/024808 | 3/2003 |
| WO | WO 2008/145408 | 12/2008 |
| WO | WO 2010/022838 | 3/2010 |

* cited by examiner

*Primary Examiner* — Gregory J Toatley
*Assistant Examiner* — Jarreas C Underwood
(74) *Attorney, Agent, or Firm* — Occhiuti & Rohlicek LLP

(57) ABSTRACT

An apparatus comprising a container handling device comprising a centering device having a standing surface and a container gripper having a head side, a foot side, inspection openings on both said head side and said foot side, light-conducting elements, and a gripper bell having an inner area, a light source arranged to couple light into said light-conducting elements, a detection-and-control system comprising an optical system, and wherein said inner area can be illuminated by emerging light so that a cover side arranged at said foot side can be inspected by said optical system through said container gripper and by said light-conducting elements.

17 Claims, 5 Drawing Sheets

COVER VIEW GRIPPER

CROSS REFERENCE TO RELATED APPLICATION

This application is the national phase filing of international application no. PCT/EP2010/007501, filed Dec. 9, 2010, which claims the benefit of the priority date of German application no. 10 2010 012 214.9, filed Mar. 19, 2010. The contents of the aforementioned applications are incorporated herein in their entirety.

FIELD OF INVENTION

The invention concerns a container handling device, and in particular, a labeling device for bottles, containers etc., that comprises at least one centering device with a standing surface and a container gripper, wherein at least one detection-and-control system is provided comprising at least one optical system. The invention also concerns a method for inspection, in particular a method for cover seat inspection.

BACKGROUND

DE 3 308 489 A1 describes a centering device for upright vessels, in particular in labeling machines, with a standing plate that is mobile downwards against a spring force from an upper end position that is fixed by a stop. The standing plate is surrounded by a centering ring that has a hopper-like centering surface adapted to the vessel's cross section. A centering bell can be raised and lowered by a control device. The vessels are pressed against the standing plate and centering ring by the centering bell.

To achieve a precise centering and constant height position of the vessel base, DE 3 308 489 A1 proposes that the standing plate comprise a lower end position fixed by a stop, that the centering ring be mounted mobile in height and against a spring force downward from an upper end position defined by a stop, and that the control device for the centering bell be formed such that the standing plate reaches its lower end position when the vessel is lowered.

Vessels or containers can, for example, be used as bottles for fluids, and in particular, for drinks. The containers, e.g. bottles, can be made from a transparent or translucent material, for example glass or a translucent plastic, such as PET. It is, however, also conceivable that the containers comprise other materials and that they are filled with other products.

The filled containers are supplied to the container handling device cited initially, e.g. a labeling machine. At an alignment station, before labeling, the containers are twisted into a particular position so that the labels are always arranged at the same position on the respective container. This is achieved by having the alignment station include one or more detection systems that detect design features, such as embossed features, on the container, in relation to which the labels or other markings are intended to be oriented and positioned precisely. As a result, the entire periphery of the container is detected. The containers pass by the detection system while mounted rotating on the standing surfaces, e.g. as turntables. After having passed the detection system or systems, the containers are twisted by the turntable into the desired position according to a signal generated by the detection system. When the container is correctly aligned, it is labeled so that the labels are preferably always oriented in the same way and as desired in relation to the design features, e.g. the embossed features.

Before labeling, the container is closed by a closer element in a container-handling device, which in one embodiment is a closing machine. The examplary closing machine can also comprise a turntable and a container gripper with which the container is securely held upright.

It is conceivable that, on its cover, the closer element will have a decorative or identification mark, such as a logo of a drink manufacturer. It has been shown in practice that when closer elements that have identification logos arranged on the cover are applied at random in relation to the design features of the container and also the label, i.e. quasi-twisted, the result is an overall disruptive picture of the container compared with that of the same container in which the closing element has been aligned carefully.

There are, however, containers that do not have any design features, such as embossed features, so that alignment of the container in relation to a constant arrangement of labels or similar marks is not required. Hence the labels are arranged differently on each container in a disadvantageous manner. Viewed overall with the closer elements, which are also not aligned to the labels or similar markings, the total impression left on the consumer is very disruptive. The appearance of the container is disturbed and the user's perception is adversely affected. This is reinforced, in particular, if the closer element carries logos that, like the example labels, indicate, for example, the producer of the container contents or the actual container contents.

The detection system or systems are designed as separate inspection devices that, under some circumstances, increase the construction size of the container-handling device. This is disadvantageous because of the usually limited space available. By means of a separate inspection device the position of the cover on the container is also monitored. Namely it is possible for the closer element to be seated incorrectly, i.e. so that it does not close the container correctly. To this extent the containers are also subject to a quality control.

SUMMARY

The invention seeks to provide a container-handling device and a method of the type cited initially with simple means so that closure inspection is possible directly at the container-handling device, while avoiding the disadvantages associated with construction space.

According to the invention, this object is achieved by a container handling device in which the container gripper has inspection openings on both the head and the foot side, at least one light source is provided, and the container gripper is formed of at least partially light-conducting or comprises at least light-conducting elements, so that a surface, in particular a cover surface, can be inspected by the optical system through the inspection openings and by means of the light-conducting design or light-conducting elements, an illuminated inner area can be inspected.

Advantageously, the invention provides a hollow-shaft container-gripper that, in cooperation with the light-conducting element or the light-conducting design with the light source, "radiates" at least in regions. Also suitably a plate opening is provided in the preferably fixed header plate, corresponding to the optical system. Thus the optical system, which in some embodiments is a camera, can "look" from above through the header plate (plate opening) and the container gripper onto the advantageously evenly-illuminated inner area of the container gripper, e.g. onto the closer element or the illuminated cover, and record its position. A further advantage in relation to the optical system arranged above the header plate is that, in this way, the construction width, i.e. the radial extent of the container-handling device is not adversely affected, i.e. not increased. In an image-processing-and-control-unit connected with the optical system, quality control is provided by verifying the closing effect of the closer element and also the position of the closer element in relation to the labels or printing to be applied to the container concerned. For this, the image-processing-and-control unit generates a corresponding signal for positioning either the container or the closer element in the necessary position.

In the case of a closing machine, the closer element first laid on a bottle opening can be aligned by the container gripper. It is, however, also possible for the container to be modified in its position, e.g. twisted, in relation to the closer element. The same applies for both the labeling machine and for the closing machine.

It is also conceivable to store the position of the closer element allocated to the container concerned, and, for example, to pass the corresponding signal to a subsequent alignment station that aligns the closed bottle according to decoration on the closer element, using, for example, a turntable or container gripper. The alignment station can be allocated to a labeling machine, in which each turntable with an allocated container gripper can perform a corresponding alignment. A signal could also be transmitted to eject containers with incorrectly seated closer elements.

In a preferred embodiment, the optical system or camera is arranged to be stationary on the container-handling device, i.e. for example, on the closing machine and/or on the labeling machine, so that containers to be inspected pass the optical system relative to optical system or camera. For example, a single optical system suffices if this is arranged at a labeling machine, e.g. in the embodiment as a labeling carousel, wherein evidently all container grippers of the labeling carousel should be designed as hollow-shaft container-grippers.

In a preferred embodiment, it can be provided that the at least one light source is arranged to be stationary. It is suitable if the light source is arranged in relation to the passing container gripper such that the gripper bell is irradiated by the light source. The light source in this embodiment can be arranged laterally radially inside and/or radially outside on at least on one side, preferably on several sides, in relation to a central axis of the labeling carousel, wherein possibly several light sources can advantageously have the multi-sided arrangement. To this extent, the light source is suitably arranged in relation to the central axis of the container-handling device between the central axis and the passing container grippers so that advantages of construction space can also be achieved. In one embodiment, the gripper bell is designed as a light-conducting element that transmits light introduced radially from the side such that the inner area of the gripper bell is preferably evenly illuminated. The gripper bell can, for example, be formed, at least partially or completely, from a transparent material, such as Poly(methyl methacrylate), which is sold under the name PLEXIGLAS (R)) or polycarbonate, which is sold under the name MACROLON(R), to name just some non-restrictive material examples.

It is also possible that the gripper bell, whether partially or completely transparent, has at least partially non-convex surfaces for optimum light inlet. In one embodiment, the gripper bell is a polyhedral-conical body.

Some embodiments use a correlating light arrangement, for example a concave light field, to achieve an optimum light inlet and maximum evenness or scatter at the outlet side. It is also possible for a diffuser provided on the inner surface of the gripper bell to output the introduced light to achieve further improvement in the homogeneous illumination.

The light sources can, for example, be LED's and/or other suitable light sources that can be controlled or pulsed with overcurrent in synchrony with the image recording, i.e. the optical system, or lit constantly. Preferably the light source and the optical system, i.e. the camera, are coupled together via the image-processing-and-control unit so that the camera always records an illuminated closer element, and so that the light source is lit or emits a light flash in synchrony with the image recording.

In a further possible embodiment the hollow-shaft container-gripper can have a light-conducting element arranged in its interior. In this advantageous embodiment the light-conducting element extends from the head side of the container gripper towards the foot side. On the head side the light source can be arranged preferably lying directly on the light-conducting element, wherein the light source is preferably designed as a closed ring light illumination (preferably LED) which is described in more detail below. From the head side in the direction of the foot side, the light-conducting element preferably has a cover that ends before the foot side to form a protrusion of the light-conducting element from which the introduced light emerges and the inner area of the container gripper i.e. the inner area of the gripper bell can be illuminated preferably evenly.

The light element can be formed as a light-conducting tube of a suitable light-conducting material such as for example Plexiglas. A fiber bundle is also conceivable as a light-conducting element.

To avoid emergence of light from the light-conducting elements towards the outside or towards adjacent container grippers, the light-conducting element on its outside can have a cover that, at the foot side, terminates preferably flush with the light-conducting element.

In a preferred embodiment a light source is allocated to each container gripper, wherein again only a single optical system or camera is sufficient, which preferably is arranged to be stationary on the container-handling device. Here too, it is advantageous that the light source be a ring light illumination that does not increase the space required for the container-handling system.

In the foregoing embodiments, the light source, which is a ring light illumination, is arranged at the head side of the light-conducting element such that the emitted light is coupled directly into the light-conducting element evenly all round. By means of the light-conducting element, the light is passed into the area of the gripper bell where the light emerges radially inwards. In the foot area of the light-conducting element, the light-conducting element can be ground or have a prism to achieve light scattering, thus further improving the homogeneous illumination. In addition, the inner surface of the light-conducting element, or its protrusion and/or the prism, can be coated with a diffuser or other suitable light scattering element.

The optical system is preferably arranged to be stationary above the container gripper. In a preferred embodiment, a collimator is allocated to the optical system or camera. Also the container gripper can have at least one lens in order to create the required light beam path of the optical system or camera. It is favorable for one lens to be arranged at the head and for another lens to be arranged at the foot.

It is also suitable for a damping element to be arranged on the gripper bell or on the corresponding contact surface that contacts the closer element. In the simplest design, the damping element is an O-ring. The gripper bell is designed such that it contacts the closer element on its side surface to ensure a fault free "view" of the camera onto the cover side of the closer element. The damping element can be made of white or transparent resilient plastic. Several web or circular damping elements can also be provided.

Each container gripper has a drive system that, in a preferred embodiment, acts on the outside of the container gripper, for example in the embodiment as a magnetic direct drive, in order to drive the gripper by means of a reciprocating and/or rotary drive.

Advantageously it is provided that, in a closing machine, the closer element is placed on a mouth opening of the container or bottle. The container or bottle is transported or delivered to the labeling machine or labeling device. The labeling device aligns the containers are aligned, preferably using the container gripper. The cover seat inspection can advantageously take place through the hollow container gripper so that alignment takes place on the basis of a comparison between the actual image recorded or actual data and nominal data. Before the last two steps, a rough alignment can take place. The container gripper and/or parts thereof are brought to radiate by light introduction so that the inner area is illuminated.

BRIEF DESCRIPTION OF THE FIGURES

Further advantageous embodiments of the invention are disclosed in the sub-claims and the following description of the figures, in which:

In the various figures, the same parts always have the same reference numerals so these are usually only described once.

DETAILED DESCRIPTION

Figure 1:
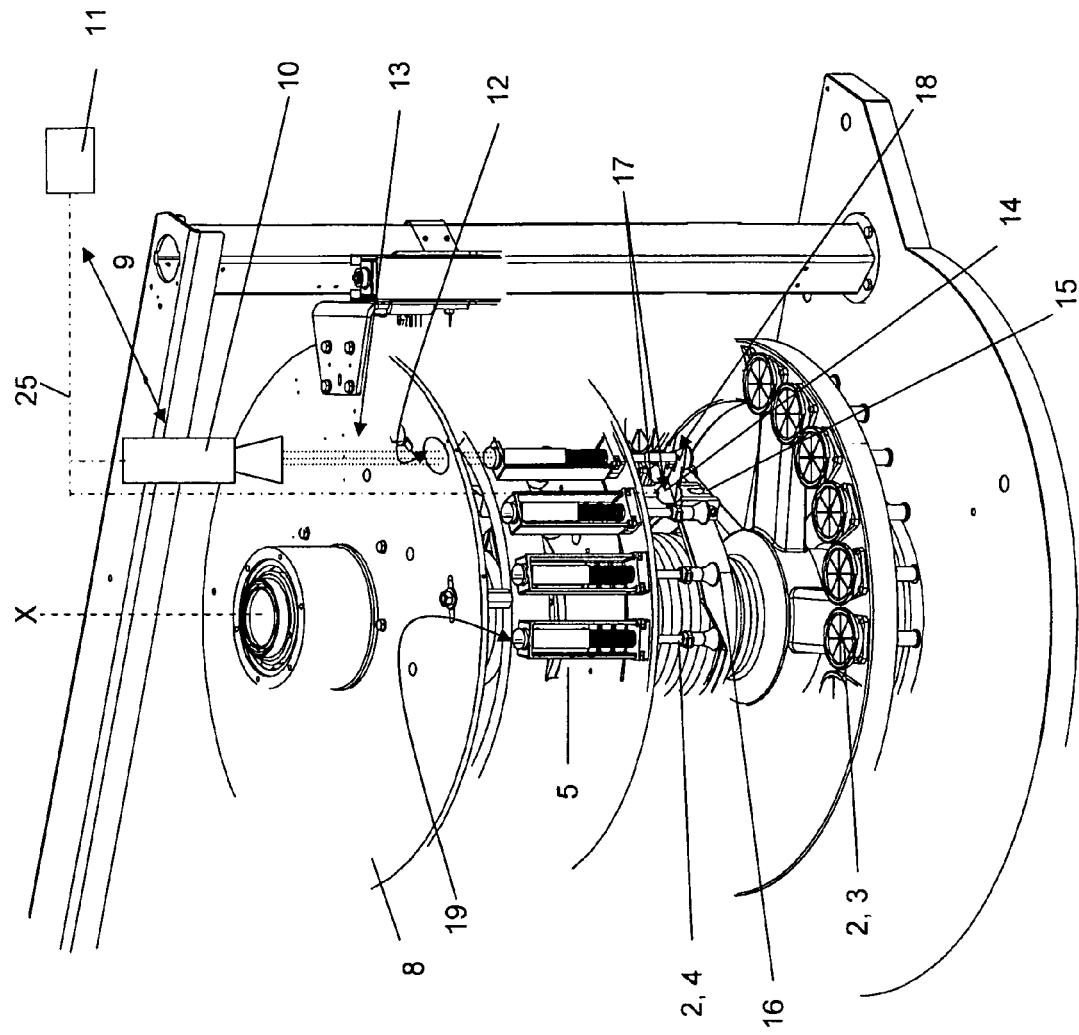
FIG. 1 is a perspective part view of a container-handling device.

FIG. 1 shows a container-handling device 1 in an example embodiment as a labeling machine or a labeling carousel. The container-handling device 1 has several centering devices 2, each with a standing surface 3 and a container gripper 4.

Figure 2:
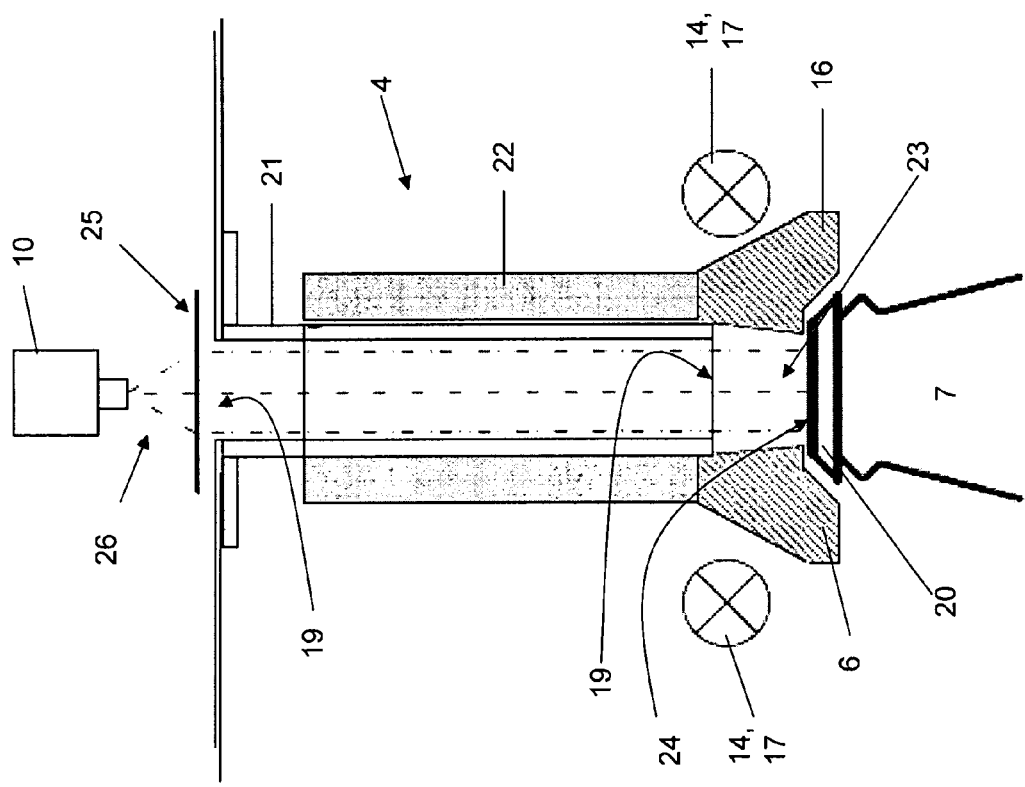
FIG. 2 is a longitudinal section of a container gripper.
Figure 3:
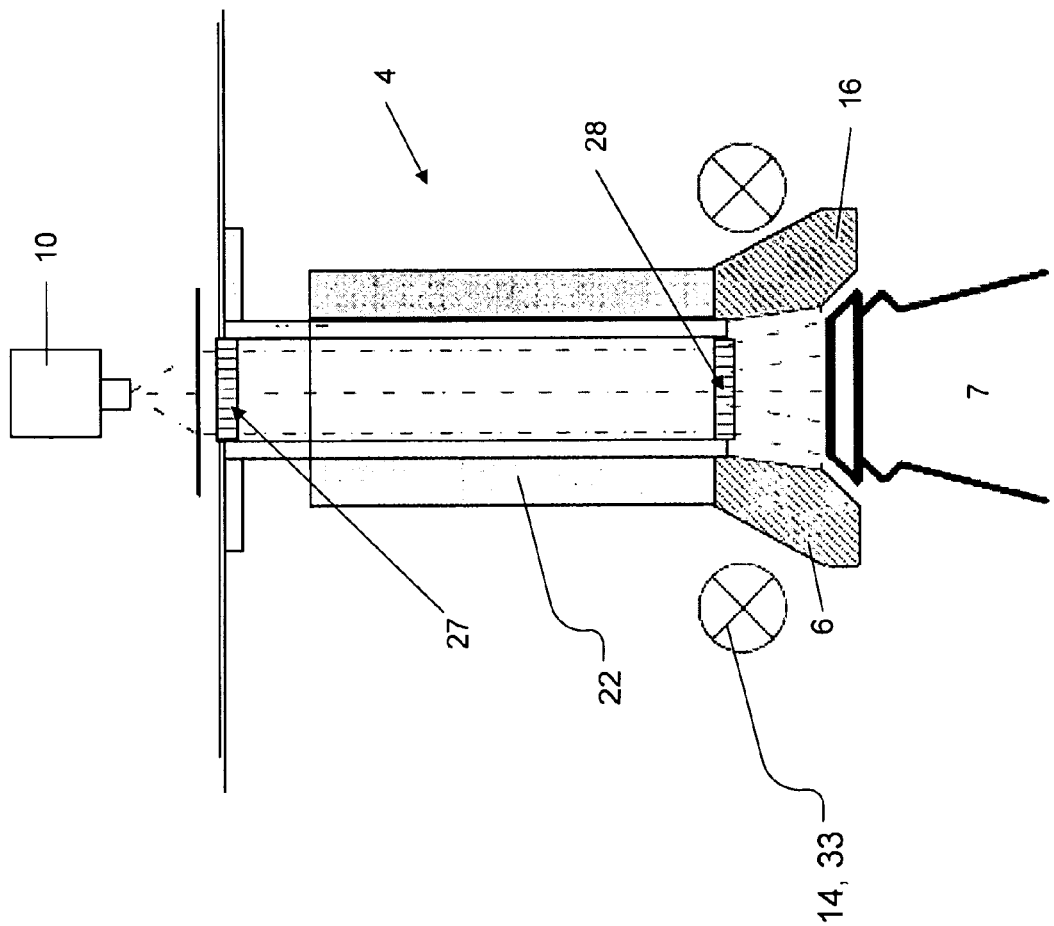
FIG. 3 shows the container gripper of FIG. 2 with lenses arranged thereon.
Figure 4:
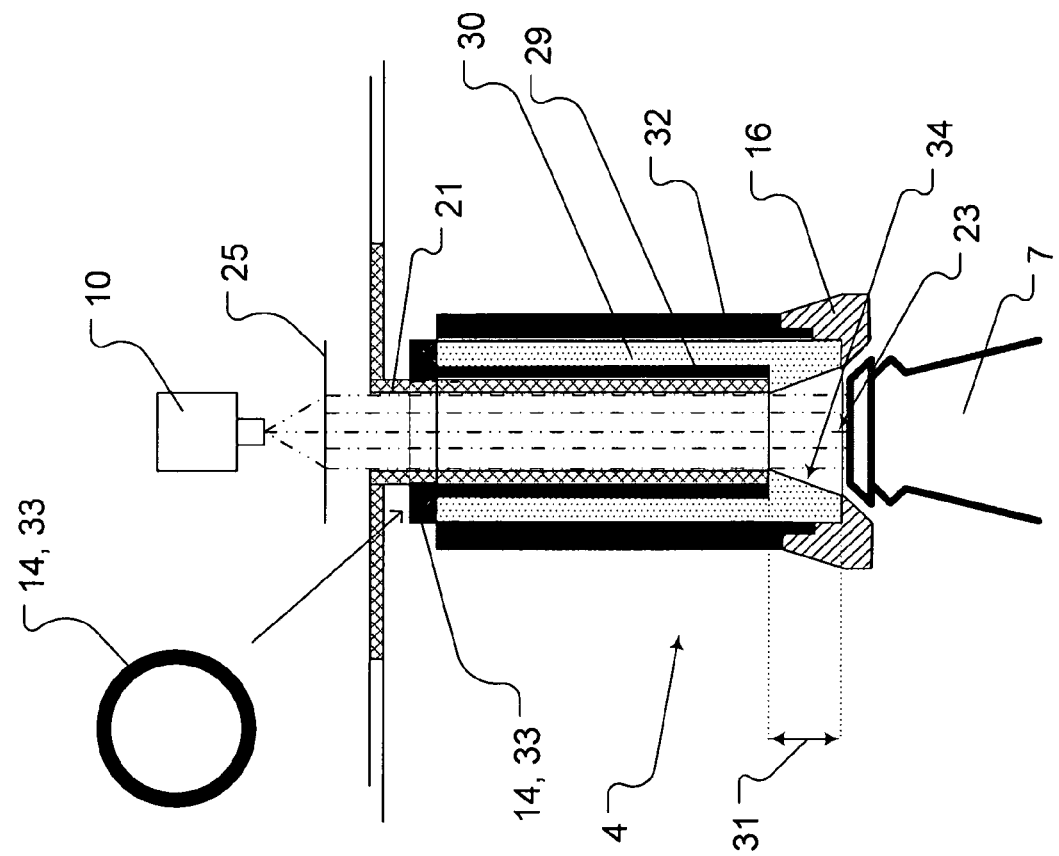
FIGS. 4 and 5 show longitudinal sections of further embodiments of a container gripper.

The standing surface 3 is designed in the known manner as a turntable 3. The container gripper 4 is mounted on a drive device 5 so that it can be raised and/or rotated. The centering devices 2 rotate the containers 7 (FIGS. 2 to 4), for example bottles, about a central axis X of the container-handling device 1 and, for example, supply them to labeling machines. The containers 7 stand with their foot on the respective turntable 3 and are held at their head by the container gripper 4. FIGS. 2 to 4 show the containers 7 or bottles merely in extract at their neck area.

The container-handling device 1 has a fixed header plate 8 and a detection and control system 9 that comprises an optical system 10, which, in the present embodiment includes a camera 10, and an image-processing-and-control unit 11.

The optical system 10 is arranged to be stationary on the container-handling device 1 in the drawing plane above the header plate 8, and is suitably fixed. Corresponding to the arrangement of the optical system 10, in the header plate 8 is a plate opening 12 that enables the optical system 10 to look through the header plate 8 from above onto the container gripper 4, as shown by means of lines 13.

The beam path of the optical system 10 through the container gripper 4 is shown in FIGS. 2 to 4. It is essential that, with the optical system 10 arranged above the header plate 8, closure views or cover seat inspections are possible through the plate opening 12 and through the container gripper 4, for which in the best case which a single stationary optical system 10 or single stationary camera 10 is required in order to obtain the closure views of the passing containers 7. In FIG. 1 further centering devices 2 of the container-handling device 1 are not shown for the sake of clarity.

The container handling device 1 comprises a stationary light source 14 that is arranged on a fixing device 15 and designed such that a gripper bell 16 of the container gripper 4 is illuminated when it passes the light source 14. To achieve this, the light source 14 has two lighting means 17 arranged at the side of the gripper bell 16, each of which can emit a pulsed light beam 18, shown in FIG. 1 as a light flash 18. The fixing device 15 is preferably designed to be fork-like with two fork webs, on each of which is arranged a lighting means 17 corresponding to the gripper bell 16. The respective lighting means 17 generates the light flash 18 quasi-laterally to the passing gripper bell 16 and indirectly illuminates the gripper bell 16.

As FIG. 2 shows, the respective container-gripper 4 is designed as a hollow-shaft container-gripper 4 that has inspection openings 19 on both the head and the foot side, i.e. in the area of the container bell 16. To this extent, the optical system 10 or camera 10 can look from above, through the header plate 8, and through the hollow shaft container gripper 4 onto a closer element 20. In the illustrated embodiment, the closer element 20 is a crown cap, which at its side, i.e. at its oblique outer surface, is in contact with the gripper bell 16. FIG. 2 does not show this contact for the sake of clarity.

The gripper bell 16 is made at least partially, and in some cases, completely, from a transparent material. A suitable transparent material is, for example, a transparent plastic such as polycarbonate or PMMA, sold under the names MACROLON(R) and PLEXIGLAS(R) respectively. The container gripper 4 has a gripper holder 21 that comprises a plastic tube 22.

If now the corresponding container gripper 4 passes the light source 14 and the optical system 10, the lighting means 17 emits the light flash 18 so that the emitted light is coupled radially laterally into the gripper bell 16. The gripper bell 16 is advantageously designed as a light-conducting element 6 or is made from light-conducting material so that the light introduced therein is emitted at the inner surface of the gripper bell 16 and illuminates the inner area 23 of the gripper bell 16. Thus, the optical system 10 can view the illuminated cover side 24 of the closer element 20 and take a corresponding picture. To achieve this, the light source 14 and optical system 10, i.e. the camera 10, are connected via the image-processing-and-control unit 11, as indicated by dotted line 25. This ensures, for example, that the light flash 18 and image recording can be synchronized, i.e. that an image can be recorded while the closer element 20 is illuminated. For example, on the cover side 24, one can place a decorative element or other design feature. The actual image recorded by the optical system 10 is passed to the image-processing-and-control unit 11, in which the images or image data supplied are analyzed. The images or image data supplied are processed, for example, by comparison with the nominal data stored in the image-processing-and-control unit 11. The image-processing-and-control unit 11 is, for example, a computer or a computer-controlled unit with corresponding inputs for analog or digital data supplied by the optical system 10. Furthermore the image-processing-and-control unit 11 has an output, not shown, that, for example, can be connected with the drive device 5 of the respective container gripper 4 in order to position the container 7 in a nominal position, i.e. to achieve a corresponding twist of the container 7 held in the container gripper 4 into the desired position. It is also possible, if the image-processing-and-control unit 11 is connected with the turntable 3, to achieve a repositioning of the container 7 standing thereon. Also the image-processing-and-control unit 11 can carry out inspections with regard to seat quality of the closer element 20 on the container mouth, in order, where applicable, to be able to exclude containers 7 that have poorly seated closer elements 20 from being labeled, and to be able to eject such containers.

As can be further seen in FIG. 2, a collimator 25 is also allocated to the stationary optical system 10 or camera 10. The gripper holder 21 is designed as a hollow tube with a flange arranged on the head. The beam path 26 of the optical system 10 or camera 10 is indicated by the dotted line 26, which corresponds to the lines 13 in FIG. 1.

In FIG. 3 the hollow-shaft container-gripper 4 has lenses 27 and 28 on its head and foot side, where lens 27, which is the inlet lens 27, is arranged on the header side inspection opening 19. Both lenses 27 and 28 are arranged in the hollow shaft gripper holder 21, with the lens 28 being designed as an outlet lens 28.

A further embodiment of the hollow-shaft container-gripper 4 is shown in FIG. 4.

The hollow-shaft container-gripper 4, which is shown in longitudinal section, has, as before, a hollow gripper-holder 21 that is cylindrical. This comprises, for example, an inner protection and guide tube 29 that, on the foot side, terminates flush with the gripper holder 21. The inner protection and guide tube 29 is merely optional and comprises a plastic, whereas the gripper holder 21, as before, can be made of stainless steel. Naturally these materials should be considered merely as examples. The optional protection and guide tube 29 is surrounded by a light-conducting element 30 on its outside. The light-conducting element is designed, for example, as a Plexiglas tube. But it can also comprise a fiber bundle.

The light-conducting element 30 extends from the head side of the container gripper 4 in the direction of the opposing foot side. The light-conducting element 30 protrudes by a protrusion 31 over the lower edge of the gripper holder 21 and the optional protection and guide tube 29. The light-conducting element 30 is surrounded on the outside by an outer protective tube 32. The gripper bell 16 is connected with the outer protective tube 32. In this embodiment the gripper bell 16 can be formed of a standard material and need not be designed as a light-conducting element.

On the head side, allocated to the light-conducting element 30, is the light source 14, which in this embodiment is a ring light illumination 33. This ring light illumination can, for example, be formed as an LED crown from a multiplicity of individual LED's. The ring light illumination 33 is designed and arranged such that emitted light it couples directly into the light-conducting element 30 evenly all round on the header side. The light source 14 or ring light illumination 33 can light constantly but can also be connected with the image-processing-and-control unit 11 and thus light or flash in synchrony with the image recording of the optical system 10.

The light-conducting element 30 guides the introduced light in the direction of the protrusion 31, which emits the light and thus illuminates the inner area 23 of the gripper bell 16. To this extent the optional protection and guide tube 29 or gripper holder 21, with its cylindrical section and/or the outer protection tube 34, can also be designated a cover element or cover for the light-conducting element 30 that prevents light from emerging from the light-conducting element 30 to the inside or outside before the protrusion 31 viewed in the height direction.

As already stated, the light introduced on the head side emerges from the light-conducting element 30 to the inside at the protrusion 31. Preferably, the light is emitted here obliquely laterally by means of multiple reflections. As shown in FIG. 4, at its protrusion, the light-conducting element 30 can be ground so as to form a virtual prism 34 or scatter prism 34 in order to achieve an even illumination of the inner sector or homogeneous illumination of the closer element 30 and its decoration on the cover side. The prism 34 can also be designed as a separate element and fixed suitably to the inner face of the protrusion 31. It is also possible to coat the inner surface of the protrusion 31 or prism 34 with a diffuser material. A homogeneous illumination is particularly useful in the case of reflective surfaces.

Naturally the embodiment shown in FIG. 4 can also have lenses 27 and 28 as shown in the embodiment seen in FIG. 3.

Figure 5:
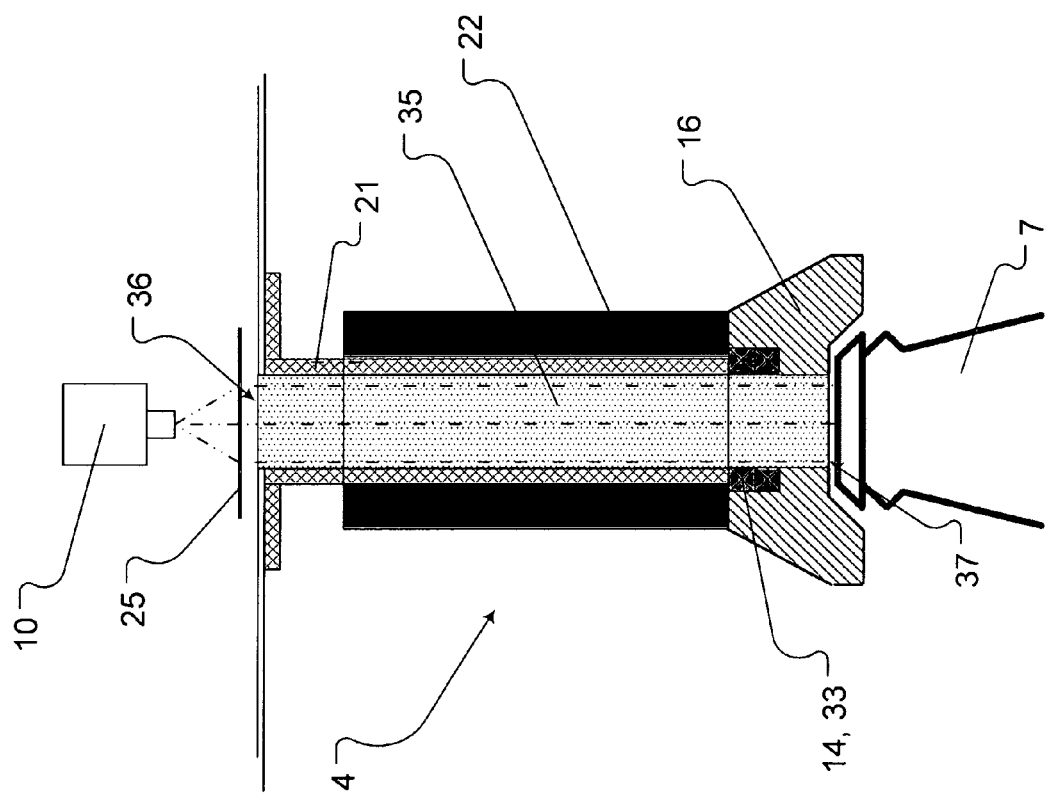

The variant shown in FIG. 5 of the device according to the invention provides an inspection cylinder 35 that is made from the same material as the cover view gripper 16 or from another suitable transparent material. In the example shown in FIG. 5, this inspection cylinder 35 does not have concave or convex properties. However, these can be provided by suitable grinding on the face sides to achieve advantageous lens effects.

The ring light illumination 33 in the variant shown is designed or arranged on several levels so that emitted light is coupled directly into the inspection cylinder 35 evenly all round on the head side. The ring light illumination 33 is connected with electrical and control systems by lines not shown. The light source 14 or ring light illumination 33 can light constantly, but can also be connected with the image-processing-and-control unit 11 in order to light or flash in synchrony with the image recording of the optical system 10. Naturally illumination can be provided which, in the same way as the example shown in FIG. 2, introduces light from the outside into the gripper bell 16 and then into the inspection cylinder 35.

For optimum light coupling into the inspection cylinder 35 and subsequent illumination of the desired examination window e.g. a crown cap 20, it may be necessary for the outer cylindrical face of the inspection cylinder 35 to be roughened or etched in the area of the ring light 33 so as to prevent reflections. In particular it is advantageous to polish the faces 36 and 37 of the inspection cylinder 35 to a high standard, e.g. by means of an electric polishing method, in order to achieve optimum optical properties. Naturally it can be provided that the gripper 16 and the inspection cylinder 35 are made in one single piece.

The advantage of the embodiment shown FIG. 5 is that no soiling or deposits can occur on the inside of the otherwise hollow container gripper 4.

The invention offers the possibility of illuminating the closer element 20, or its cover side decoration, by means of at least one light source 14 in cooperation with the respective light-conducting element 6 or 30, or with the at least partially light-conducting design of the container gripper 4 according to the invention, or with the advantageous embodiment of the container gripper 4 with light-conducting elements, wherein by means of camera 10 the image of the closer element 20, or its cover side decoration, can be recorded from above, through the header plate 8, and through the container gripper 4, in order to use the recorded image for inspection purposes. For example the container 7 can be aligned according to the cover features, and a quality control step for inspecting cover seating can be carried out. Also, the closer element 20 can be moved by means of the container gripper or gripper bell into the desired position by a closing machine.

To this extent, the container-handling device 1 is not restricted to the labeling machine described. For example the container-handling device 1 can also be designed as a closing machine in which closure inspections through a plate opening from above through the container gripper 4 are possible. In particular the individual elements of the container gripper 4, as shown in the respective examples of FIGS. 1 to 5, can be suitably combined, replaced or complemented.

LIST OF REFERENCE NUMERALS

1 Container-handling device
2 Centering device
3 Standing surface (turntable)
4 Container gripper
5 Drive device
6 Light-conducting element
7 Container
8 Header plate of container-handling device 1
9 Detection control system
10 Optical system
11 Image-processing-and-control unit
12 Plate opening in header plate 8
13 Viewing path of optical system
14 Light source
15 Fixing device for light source 14
16 Gripper bell
17 Lighting means
18 Light flash
19 Inspection openings in gripper 4
20 Closer element
21 Gripper holder
22 Plastic tube
23 Inner area of gripper bell 16
24 Cover side
25 Connections 10 and 14 with 11
26 Beam path of 10 in 4
27 Lenses
28 Lens
29 Protection and guide tube
30 Light-conducting element
31 Protrusion of light-conducting element 30
32 Outer protection tube
33 Ring light illumination
34 Prism
35 Inspection cylinder
36 Face
37 Face

The invention claimed is:

1. An apparatus comprising a container handling device comprising a centering device having a standing surface and a container gripper having a head side, a foot side, inspection openings on both said head side and said foot side, light-conducting elements, and a gripper bell having an inner area, a light source arranged to couple light into said light-conducting elements, a detection-and-control system comprising an optical system, and wherein said inner area can be illuminated by emerging light so that a cover side arranged at said foot side can be inspected by said optical system through said container gripper and by said light-conducting elements.

2. The apparatus of claim 1, wherein said optical system is arranged to be stationary.

3. The apparatus of claim 1, wherein said light source is arranged to be stationary.

4. The apparatus of claim 1, wherein said container handling device comprises a header plate having a plate opening, and wherein one of said cover side and said illuminated inner area can be inspected by said optical system through said plate opening through said container gripper.

5. The apparatus of claim 1, wherein said light source is arranged so that said light-conducting element is irradiated and said gripper bell is formed at least in part from a light-conducting material.

6. The apparatus of claim 1, wherein said light source is arranged at least on one side laterally to said light-conducting element in the design as a gripper bell.

7. The apparatus of claim 1, wherein said light-conducting element is formed from a transparent plastic.

8. The apparatus of claim 1, wherein said light-conducting element is arranged in an interior of said container gripper and extends from a head side towards an opposite foot side, and wherein said light source is arranged as a ring light illumination on said head side of said light-conducting element.

9. The apparatus of claim 1, wherein said light-conducting element on said foot side comprises a protrusion from which light introduced by said light source emerges and illuminates said inner area.

10. The apparatus of claim 1, wherein said light source and said optical system are controlled in synchrony such that said optical system always inspects an illuminated inner area.

11. The apparatus of claim 1, wherein said light source is constantly lit so that said light-conducting element constantly illuminates said inner area.

12. The apparatus of claim 1, further comprising optical lenses on at least one of said head side and foot side in an area of said inspection openings.

13. The apparatus of claim 12, further comprising a lens on said foot side for expanding light incident thereon so that a shadow area below said lens can be inspected, said shadow area having a diameter greater than a free cross section before said lens.

14. The apparatus of claim 1, wherein said inner core of said container gripper comprises an inspection cylinder made of transparent material.

15. A method for inspecting containers by a container handling device having a centering device having a standing surface and a container gripper, and a detection and control system having an optical system, said method comprising applying a closer element onto a container in a closer, transporting said container to a labeling device, using said centering device, centering said container by standing said container on said standing surface using said container gripper, using said optical system through said container gripper, inspecting a cover seat, wherein inspecting comprises illuminating an inner area of a gripper bell of said container gripper, and aligning said container according to a required nominal position.

16. The method of claim 15, further comprising carrying out a rough alignment of said container prior to at least one of aligning said container and inspecting said cover seat.

17. The method of claim 15, further comprising providing said container handling device with a header plate, said header plate having a plate opening, and wherein inspecting said cover seat comprises inspecting through said plate opening through said container gripper.

* * * * *